(12) United States Patent
Alwan et al.

(10) Patent No.: US 8,551,026 B2
(45) Date of Patent: *Oct. 8, 2013

(54) METHOD AND SYSTEM FOR THE DERIVATION OF HUMAN GAIT CHARACTERISTICS AND DETECTING FALLS PASSIVELY FROM FLOOR VIBRATIONS

(75) Inventors: Majd Alwan, Charlottesville, VA (US); Robin A. Felder, Charlottesville, VA (US); Steven W. Kell, Keswick, VA (US); Siddharth Dalal, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 277 days.

This patent is subject to a terminal disclaimer.

(21) Appl. No.: 12/977,899

(22) Filed: Dec. 23, 2010

(65) Prior Publication Data
US 2011/0190667 A1 Aug. 4, 2011

Related U.S. Application Data

(63) Continuation of application No. 10/550,157, filed as application No. PCT/US2004/009098 on Mar. 26, 2004, now Pat. No. 7,857,771.

(60) Provisional application No. 60/460,237, filed on Apr. 3, 2003.

(51) Int. Cl.
*A61B 5/103* (2006.01)
*A61B 5/117* (2006.01)
*G01C 22/00* (2006.01)
*G01B 5/02* (2006.01)

(52) U.S. Cl.
USPC ........ 600/595; 600/587; 702/160; 340/573.1; 340/573.7

(58) Field of Classification Search
USPC .......... 600/587, 592, 595; 702/142, 149, 160; 340/573.1, 566, 573.7; 367/135, 136
See application file for complete search history.

(56) References Cited

U.S. PATENT DOCUMENTS 3,296,587 A * 1/1967 Baker ........................... 367/136
3,614,724 A * 10/1971 Brown et al. ................. 367/136
3,894,437 A * 7/1975 Hagy et al. ................... 73/865.4

(Continued)

FOREIGN PATENT DOCUMENTS

JP 2000299751 A * 10/2000

OTHER PUBLICATIONS

Derwent Abstract of JP 2000-299751. Derwent. p. 1.*

*Primary Examiner* — Max Hindenburg
*Assistant Examiner* — John Pani
(74) *Attorney, Agent, or Firm* — Kilpatrick Townsend & Stockton LLP; Robert J. Decker

(57) ABSTRACT

The gait monitor system and method provides various basic gait parameters including step count, cadence, and step duration, in addition to its ability to distinguish between normal, limping and shuffling gait modes, as well as determine falls. Moreover, this gait monitor may be provided with additional sensors, e.g. beam break at the beginning and end of a corridor to estimate average walking velocity (with the distance between the beams known or determined); this enables the calculation of additional gait characteristics such as average step length and average stride length. These parameters can additionally be used to detect various gait anomalies and other diagnostic information.

20 Claims, 9 Drawing Sheets

(56) References Cited

U.S. PATENT DOCUMENTS

| | | | |
|---|---|---|---|
| 4,110,730 A * | 8/1978 | Varecka et al. | 367/135 |
| 4,121,192 A * | 10/1978 | Wilson | 367/129 |
| 4,214,485 A * | 7/1980 | Berger et al. | 73/655 |
| 5,081,297 A * | 1/1992 | Lebel et al. | 710/104 |
| 5,831,937 A * | 11/1998 | Weir et al. | 367/128 |
| 6,006,165 A * | 12/1999 | Okada | 702/96 |
| 6,515,586 B1 * | 2/2003 | Wymore | 340/541 |
| 7,857,771 B2 * | 12/2010 | Alwan et al. | 600/595 |
| 2002/0107649 A1 * | 8/2002 | Takiguchi et al. | 702/75 |
| 2002/0132092 A1 * | 9/2002 | Wagner | 428/192 |

* cited by examiner

METHOD AND SYSTEM FOR THE DERIVATION OF HUMAN GAIT CHARACTERISTICS AND DETECTING FALLS PASSIVELY FROM FLOOR VIBRATIONS

RELATED APPLICATIONS

This application is a continuation of U.S. Non-Provisional application Ser. No. 10/550, 157, filed on Sep. 20, 2005 now U.S. Pat. No. 7,857,771, which is a national stage filing of International Application No. PCT/US2004/009098 filed Mar. 26, 2004 which claims benefit under 35 U.S.0 Section 119(e) of the earlier filing date of U.S. Provisional Application Ser. No. 60/460,237, filed on Apr. 3, 2003, entitled "Method and System for the Derivation of Basic Human Gait Characteristics and Detecting Falls Passively from Floor Vibrations," of which the entire disclosures are hereby incorporated by reference herein.

BACKGROUND OF THE INVENTION

Gait analysis has many applications ranging from rehabilitation to sports medicine, orthopedics and studying the effectiveness of prosthetics to improve their design. See Joseph C, Andrew G., "Gait Analysis in the Amputee: Has it Helped the Amputee or Contributed to the Development of Improved Prosthetic Components?" Gait Posture (1996) 4, 258-68, of which is hereby incorporated by reference herein in its entirety. Long-term in-home gait monitoring not only can provide a measure of a person's functional ability, but it also can provide a measure of activity levels and may therefore help 'evaluate' a person's health over a long period of time. Passive in-home gait monitoring can be useful for assessing healing/deterioration following therapeutic interventions including surgeries, drug or physical therapy. Moreover, the ability to identify negative trends of subtle changes in a person's gait can contribute to detection of health problems at early stages of disease onset. Research also indicates that certain gait characteristics can be used as a biometric for identification purposes. See Little J, Boyd J., "Recognizing People by Their Gait: the Shape of Motion," Videre, Winter 1998, of which is hereby incorporated by reference herein in its entirety. See Orr R, Abowd G., "The Smart Floor: A Mechanism for Natural User Identification and Tracking Conference on Human Factors in Computing Systems," April 2000, of which is hereby incorporated by reference herein in its entirety.

On the other hand, falls are a major cause of morbidity in the elderly. See François P, Hélène C, Réjean H, David W., "Gait in the Elderly," Gait and Posture (1997) 5(2), 128-135, of which is hereby incorporated by reference herein in its entirety. They are responsible for 70 percent of accidental deaths in persons 75 years of age and older. The elderly, who represent 12 percent of the population, account for 75 percent of deaths from falls. See George F., "Falls in the Elderly," American Family Physician, April 2000, of which is hereby incorporated by reference herein in its entirety. The considerable cost involved in the treatment and Hospitalization of fall injuries and even death due to falls could be greatly reduced if falls could be predicted and avoided through appropriate intervention. An in-home gait-monitoring tool with the ability to distinguish between normal walking and abnormal gait may help predict a propensity for injurious falls. See Stalenhoef P A, Diederiks J P, Knottnerus J A, Kester A D, Crebolder H F., "A Risk Model for the Prediction of Recurrent Falls in Community-Dwelling Elderly: a Prospective Cohort Study," J Clin Epidemiol 2002 November; 55(11):1088-94, of which is hereby incorporated by reference herein in its entirety. See Azizah Mbourou G, Lajoie Y, Teasdale N., "Step Length Variability at Gait Initiation in Elderly Fallers and Non-Fallers, and Young Adults," Gerontology. 2003 January-February; 49(1):21-6, of which is hereby incorporated by reference herein in its entirety.

Human gait analysis entails numerous parameters that can be classified into spatio-temporal, kinematic and kinetic characteristics. Spatio-temporal parameters include average walking velocity, stride length, step length, step time, cadence, stance phase time, swing phase time, single support (when only one foot is in contact with the floor), double support (when both feet are in contact with the floor), and stride width. Kinematic parameters study the angles between the ankle, hip and knee joints. Finally, kinetic analysis examines moments, energy and power at these joints. See Craik R, Oatis C., "Gait Analysis Theory and Application," Mosby 1995, of which is hereby incorporated by reference herein in its entirety.

Most gait analysis laboratories use visual means for gait analysis where kinematic (See Dockstader S, Tekalp A., "A Kinematic Model for Human Motion and Gait Analysis," Proc. of the Workshop on Statistical Methods in Video Processing (ECCV), Copenhagen, Denmark, 1-2 Jun. 2002, pp. 49-54, of which is hereby incorporated by reference herein in its entirety) and biomechanical models (See Simon J, Metaxiotis D, Siebel A, Bock H, Döderlein L., "A Multi-Segmented Foot Model," 6th Annual Gait and Clinical Movement Analysis'Meeting, Shriners Hospitals for Children, Northern California, of which is hereby incorporated by reference herein in its entirety) are built from visually acquired gait data. A review of the various visual human motion and gait analysis techniques can be found in the Aggarwal J, and Cai Q. article (See Aggarwal J, Cai Q., "Human Motion Analysis: A Review," Proceedings, IEEE Nonrigid and Articulated Motion Workshop, June 1997, of which is hereby incorporated by reference herein in its entirety.) and Gavrila D. article (See Gavrila D., "The Visual Analysis of Human Movement: A Survey," Computer Vision and Image Understanding, 73(1): 82-98, January 1999, of which is hereby incorporated by reference herein in its entirety.) An excellent overview of in-the-lab gait analysis tools, methods and applications in rehabilitation can be found in the DeLisa J. article (See DeLisa J., "Gait Analysis in the Science of Rehabilitation," VARD Monograph 002, 1998, of which is hereby incorporated by reference herein in its entirety). Gait lab equipment and analysis techniques yield excellent and detailed gait characteristics and enable clinicians to prescribe an appropriate intervention. However, the equipment required for a functional gait laboratory is extremely expensive, in the range of tens of thousands to a few hundred thousand dollars in equipment and software. Additionally, the computational power required for the image based analysis make longitudinal in-home gait monitoring using these technologies impractical. Moreover, people are normally referred to gait labs for full gait analysis only after the changes in their gait have become obvious. Gait Laboratories also use pressure measurement systems such as force plates for gait analysis. Force plate data can reveal important information such as a quantitative evaluation of the effect of Total Knee Arthoplasty (TKA) in patients with osteoarthritis. See Otsuki T, Nawata K, Okuno M., "Quantitative Evaluation of Gait Pattern in Patients With Osteoarthritis of the Knee Before and After Total Knee Arthoplasty. Gait Analysis Using a Pressure Measuring System," Journal of Orthopaedic Science, 4(2): 99-105, 1999, of which is hereby incorporated by reference herein in its entirety. The pressure system measured Stance phase timing and forces. However, research at the Ohio State University demonstrated that force plate size influenced valid gait data acquisition (See Oggero E, Pagnacco G, Morr D R, Berme N., "How Force Plate Size Influences the Probability of Valid Gait Data Acquisition," Biomedical Sciences Instrumentation, 35:3-8 1999, of which is hereby incorporated by reference herein in its entirety) and that some subjects must alter their gait for valid gait data acquisition (See Oggero E, Pagnacco G, Morr D R, Simon S R, Berme N., "Collecting Valid Data From Force Plates: How Many Subjects Must Alter Their Gait?" North American Congress on Biomechanics 2000, of which is hereby incorporated by reference herein in its entirety).

Current outside the lab gait analysis techniques broadly fall under three categories depending upon the type of device used, wearable devices, walk on devices and visual gait analysis tools and techniques. Wearable devices include actigraphs and devices such as that described in the gait activity monitor to Smith et al. (See U.S. Pat. No. 5,485,402 to Smith et al., entitled "Gait Activity Monitor," of which is hereby incorporated by reference herein in its entirety.) These devices measure acceleration resulting from movement of the body or limb that may not necessarily correspond to walking. Moreover, accelerometers do not provide enough information to enable the evaluation of the actual characteristics of the gait. The gait activity monitor described in Weir et al. (See U.S. Pat. No. 5,831,937 to Weir et al., entitled "Portable Ranging System for Analyzing Gait;" of which is hereby incorporated by reference herein in its entirety.) is worn on the ankle with built-in optical communication. Another variation on this type of devices is described in Portable Ranging System, where a combination of ultrasound and infrared is used to periodically determine the distance between a person and a base station (See U.S. Pat. No. 5,623,944 to Nashner, entitled "Method for Characterizing Gait," of which is hereby incorporated by reference herein in its entirety; this device is mainly used to measure velocity). Walk-on gait analysis devices include treadmills (See U.S. Pat. No. 5,952,585 to Trantzas et al., entitled "Portable Pressure Sensing Apparatus for Measuring Dynamic Gait Analysis and Method of Manufacture;" of which is hereby incorporated by reference herein in its entirety), mats (See U.S. Pat. No. 6,360,597 B1 to Hubbard, Jr., entitled "In-Shoe Remote Telemetry Gait Analysis System, of which is hereby incorporated by reference herein in its entirety), special shoes (See Classification of Gait Abnormalities: http://guardian.curtin.edu.au/cga/faq/classification.html, of which is hereby incorporated by reference herein in its entirety), and specially designed floors (See Orr R, Abowd G., "The Smart Floor: A Mechanism for Natural User Identification and Tracking Conference on Human Factors in Computing Systems," April 2000, of which is hereby incorporated by reference herein in its entirety). The treadmill described in 'Method for characterizing gait' (See Gavrila D., "The Visual Analysis of Human Movement: A Survey," Computer Vision and Image Understanding, 73(1): 82-98, January 1999, of which is hereby incorporated by reference herein in its entirety.) has transducers mounted below the movable surface that can measures force from each foot individually can differentiate between walking and running. Arrays of pressure sensors are placed under a flexible mat sheet are described in (See U.S. Pat. No. 5,952,585, of which is hereby incorporated by reference herein in its entirety.) to measure force and other gait parameters. Another approach (See U.S. Pat. No. 6,360,597, of which is hereby incorporated by reference herein in its entirety), describes an in-shoe pressure sensing system with an external telemetry transmitter. The pressure sensor data is transmitted to a remote computer for analysis. Another potential method for gait analysis is to have a 'smart floor' comprising force plate tiles or embedding load cells under individual tiles (See Orr R, Abowd G., "The Smart Floor: A Mechanism for Natural User Identification and Tracking Conference on Human Factors in Computing Systems," April 2000, of which is hereby incorporated by reference herein in its entirety.) to measure characteristics of footsteps; this approach is expensive.

BRIEF SUMMARY OF INVENTION

The present invention passive gait monitor system and method described in this disclosure are based on detecting vibrations generated by a person or animal walking on the floor. An embodiment is implemented using an ultra sensitive optic-fiber sensor that is capable of tens of feet away from the sensor on both carpeted and uncarpeted wooden and concrete floors. However, the methods described can be applied to other vibration, acceleration, and/or deflection sensors and sensing technologies, including but not limited to piezoelectric, electromechanical, optic, laser, and fiber optic sensors. The vibration, acceleration, and/or deflection sensor can be fixed in a corridor or a walkway within the home environment or any desired environment, for short term and extended term monitoring of changes in gait mode and drifts in cadence that may indicate a heightened fall risk, as well as actual fall. Since it can be deployed in natural settings and the user does not need to wear any devices, walk on special surfaces or be observed by cameras, this gait monitor is completely passive and unobtrusive; hence, the "white coat" stress effect associated with a clinical test could be reduced or even totally eliminated.

The device and method can detect falls and can be augmented to automatically initiate an alert call to designated care providers or emergency services in the event of a detected fall episode followed by a period of inactivity.

Other applications include unobtrusive gait analysis in clinical settings. One can envision the deployment of such a monitor in a corridor within the clinic, where a person's gait is preliminarily evaluated as he/she enters the clinic and that the analysis report is available to the clinician by the time the patient walks into the examination room. Longitudinal data, together with more elaborate analysis techniques lead to a fall prediction model. Other data may include, for example, pattern recognition or identification determination of the subject (human or animal) being monitored. An embodiment of the sensing unit of the passive gait monitor is physically small, low-cost, and designed to transmit acquired data via hard-wired or wireless means. Thus, this embodiment of this passive gait monitor may be ideally suited to monitoring the 'natural gait' of a person during regular activity, in the home or in the clinic, to provide basic but essential gait characteristics.

Results obtained from a prototype design and detection algorithms applied to recorded raw sensor data demonstrate that this device provides a wide range of different applications, including biometrics.

An aspect of an embodiment of the present invention provides a gait monitoring for monitoring gait characteristics of a subject. The system comprising: a sensor module that detects floor acceleration, vibration, and/or deflection to provide acceleration, vibration, and/or deflection signal; and a processor module that analyzes the acceleration, vibration, and/or deflection signal for determining gait characteristics.

An aspect of an embodiment of the present invention provides a method for monitoring gait characteristics of a subject. The method comprising: detecting floor acceleration, vibration, and/or deflection to provide acceleration, vibration, and/or deflection signal; and analyzing the acceleration, vibration, and/or deflection signal for determining gait characteristics.

An aspect of an embodiment of the present invention provides a computer program product comprising computer usable medium having computer logic for enabling at lease one processor in a computer system or the like to monitor gait characteristics of a subject. The computer logic comprising: detecting floor acceleration, vibration, and/or deflection to provide acceleration, vibration, and/or deflection signal; and analyzing the acceleration, vibration, and/or deflection signal for determining gait characteristics.

These and other objects, along with advantages and features of the invention disclosed herein, will be made more apparent from the description, drawings, and claims that follow.

BRIEF SUMMARY OF THE DRAWINGS

The foregoing and other objects, features and advantages of the present invention, as well as the invention itself will be more fully understood from the following description of potential embodiments, when read together with the accompanying drawings in which.

DETAILED DESCRIPTION OF THE INVENTION

The floor vibration sensor employed in any embodiment of the gait monitor can be any variety of sensor modalities including, but not limited to: magnetic coil induction; laser light reflection; changes in Plasmon surface resonance; RF; changes in light due to luminescence; Doppler radar; and/or any sensor technology that transduces the minute deflections of the floor induced by gait or falling or dropping of objects.

The slightest vibrations imparted on the active sensor element either directly or through but not limited to mechanical, acoustic or optical means yield a signal that varies in an analog of the floor vibration or displacement. The sensor element may be attached to any surface including but not limited to the floor itself, the baseboard of a wall, a wall, the ceiling, and below the floor. The sensor element may be freestanding, using displacement against moment of inertia of the system or where displacement is determined by difference between the modulating surface and another plane including but not limited to the baseboard of a wall, a wall, the ceiling, and below the floor. Various support electronics may be used to provide detection, amplification and filtering of the transduced signals.

Moreover, it should be appreciated that the vibration sensor employed in any embodiment of the gait monitor may be various optic sensors, for example such fiber optic sensors as employed in U.S. Pat. No. 6,687,424 B1 to Gerdt et al., entitled "Sensing Pad Assembly Employing Variable Coupler Fiberoptic Sensor;" U.S. Pat. No. 6,463,187 B1 to Baruch et al., entitled "Variable Coupler Fiberoptic Sensor and Sensing Apparatus Using the Sensor;" U.S. Patent Application Publication 2003/0199771 A1 to Baruch et al., entitled "Apparatus and Method for Measuring Pulse Transit Time;" of which are hereby incorporated by reference herein in their entirety. Other available fiber optic sensors may be employed as well and can be any variety of sensor modalities.

Figure 1:
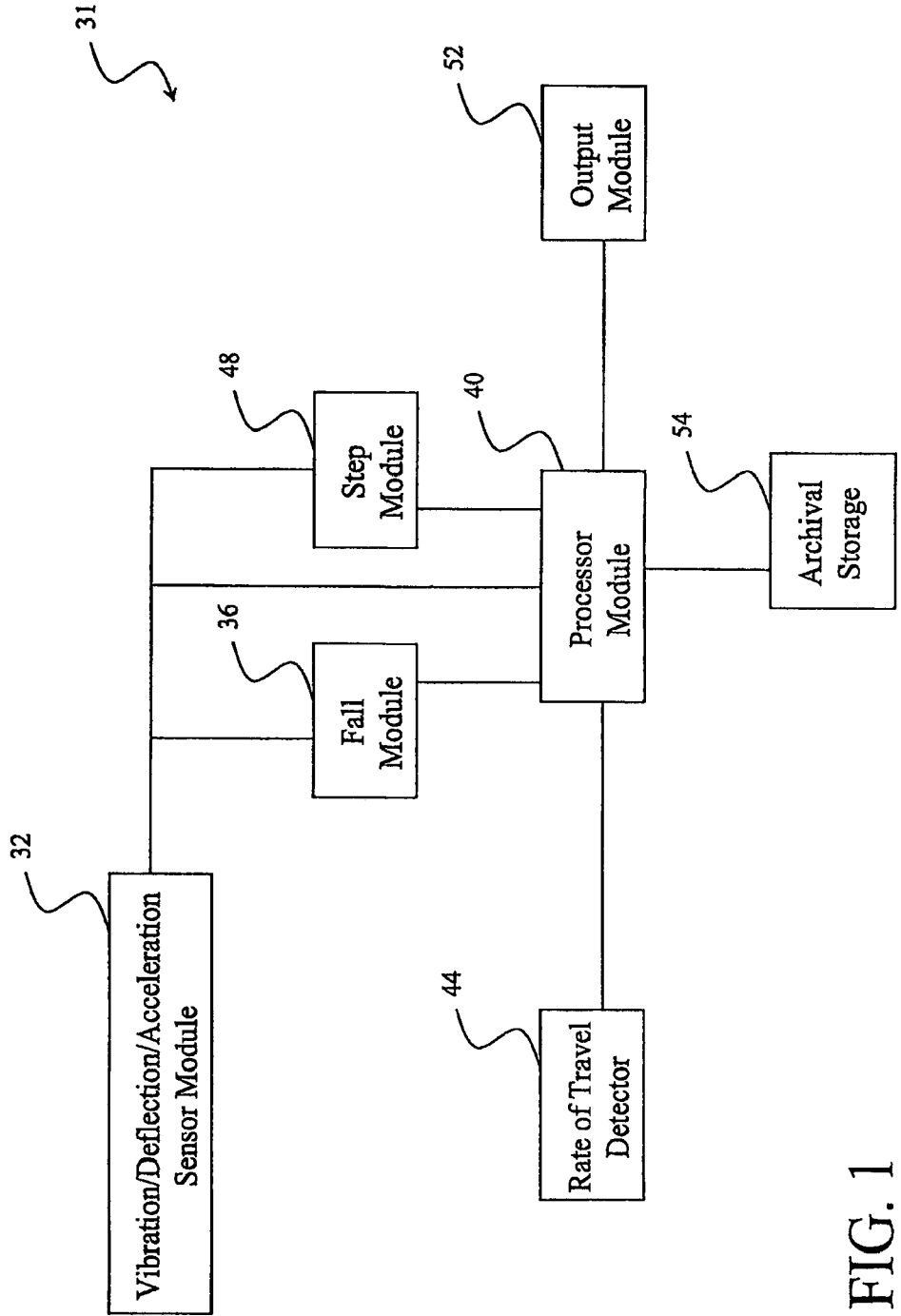
FIG. 1 is a schematic block diagram of the subject and gait monitoring system.

Referring to FIG. 1, the sensing unit or module 32 is configured so that it can measure floor 35 vibrations. The sensor module 32 can pick-up floor vibrations generated by a person or subject 33 (or animate or inanimate object) walking tens of feet away (or any distance required for setting or environment) from the sensor on both carpeted and uncarpeted wooden and concrete floors (or any given platform or base). As will be discussed in greater detail below, an embodiment of the present invention system processes the raw vibration signal of the sensor system and extracts features of significance and analyzes the extracted data to provide basic gait characteristics. In an embodiment, the processor module 40 analyzes or the like performs algorithms or manipulation to differentiate between normal gait, limping and shuffling and measure step count and calculate cadence with good accuracy when the gait is normal. A rate of travel detector module 44 is provided to track the motion or travel span of the subject 33.

Figure 2:
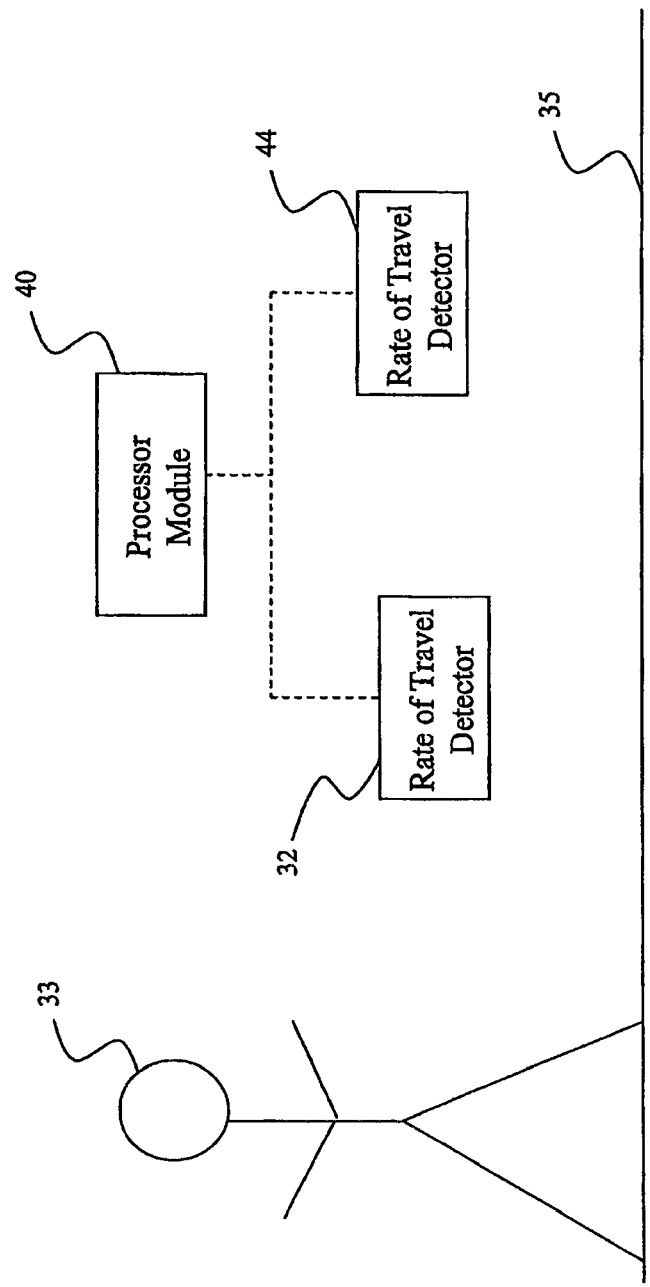
FIG. 2 is a schematic block diagram of the gait monitoring system.

Referring to FIG. 2, FIG. 2 is a schematic block diagram of the gait monitoring system and related method for monitoring gait characteristics of a subject (person, animal, animate or inanimate object). An embodiment of the present invention system 31 includes a sensor acceleration, vibration, and/or deflection module 32 that detects floor acceleration, vibration, and/or deflection to provide the acceleration, vibration, and/or deflection signal. Examples include but are not limited to magnetic coil induction; laser light reflection; changes in Plasmon surface resonance; RF; changes in light due to luminescence; doppler radar; and/or any sensor technology that transduces the minute deflections of the floor induced by gait or falling or dropping of objects. A processor module 40 is provided that analyzes the acceleration, vibration, and/or deflection signal for determining gait characteristics data obtained by the sensor module 32. The system 31 and/or processor 40 is in communication with an output module 52 for receiving the gait characteristics data. Examples of the output module 52 include at least one of the following, but not limited thereto, display, alarm, memory storage, communication device, printer, buzzer, PDA, lap top computer, computer and/or light; or any available device required for input/output. Examples of the communication device include at least one of the following, but not limited thereto, modem, pager, network interface, Ethernet card, serial communications port, parallel communications port, telephone, and/or a PCMCIA slot and card; or any other available device required for communication.

Still referring to FIG. 2, it should be appreciated that the system 31 or only portions of the system or communication paths of the system 31 (or with external devices) may be hardwired, wireless, or combination thereof. Examples of wireless communication include at least one of the following, but not limited thereto, RF link, BLUE TOOTH, an infrared, cellular phone link, optical and/or electromagnetic; or any other available wireless communication. Alternatively, the system 31 or only portions of the system or communication paths of the system 31 (or with external devices) may be hard wired, mechanical, optical, or optical-mechanical, electromechanical communication. Some examples of communication include at least one of the following, but not limited thereto, integrated circuits, wire, cable, fiber optics, a phone line, twisted pair, and/or coaxial; or any mechanism capable of communication transmission.

Still referring to FIG. 2, an embodiment of the system may include at least one rate-of-travel detector or module 44 to determine the rate of travel of the subject. For example, the rate-of-travel detector may be any one of a system of beam breaks, floor switches, and door switches or any available systems capable to track the motion, movement, or travel span of the subject. The rate-of-travel detector may operate in various modes including one of ultrasonic communication, IR communication, laser communication, ground radar communication, wide band radar communication, and/or doppler communication; or any other communication path or via necessary to effect the travel or motion detection.

Still referring to FIG. 2, an embodiment of the system may include at least one fall detector or module 36 that analyzes fall related data and at least one step module 48 that analyzes step related data. The module uses analog, digital or hybrid signal processing to reduce the raw signal for analysis and derivation of characteristics including but not limited to physical forces that are currently known in gait such as heel toe impact, heel rotation, forces generated when the toes push off the floor to get locomotion (e.g. gastricnemeous contraction), knee flexure, hip rotation, and pelvis swivel, etc. These individual force generators may be integrated into the amount of forward motion that is generated, versus the amount of motion that is spent lifting the body. The processor module 40 can provide numerous functions and operations including, but not limited to: analyzing the acceleration, vibration, and/or deflection signal for determining gait characteristics data obtained by the sensor module 32 and other components and modules of the system 31 or data or information received externally. The gait characteristics of the subject includes at least one of, but not limited thereto, step count, pace, normal condition, limp, shuffle, falls, average walking velocity, step length, and/or stride length; or any other necessary parameter required or desired for a given application.

Still referring to FIG. 2, an embodiment of the system may include at least one archival storage/memory 54. The archival storage/memory 54 stores at least one of longitudinal analysis of gait characteristics, pattern recognition, and/or identification determination; or other data as required or desired for given application. Further, the processor module 40 or other secondary processors analyzes the gait characteristics, pattern recognition, and/or identification determination data. In an embodiment the system further comprises a second processor module (not shown). The second processor module may be configured to analyze the gait characteristics, pattern recognition, and/or identification determination data; or other data as required or desired for given application.

Herein provided are illustrative embodiments to demonstrate specific examples of the present invention method and system, or components of the system. These exemplary embodiments of the system or of the individual components should be considered illustrative only rather than restrictive.

Example No. 1

Figure 3A:
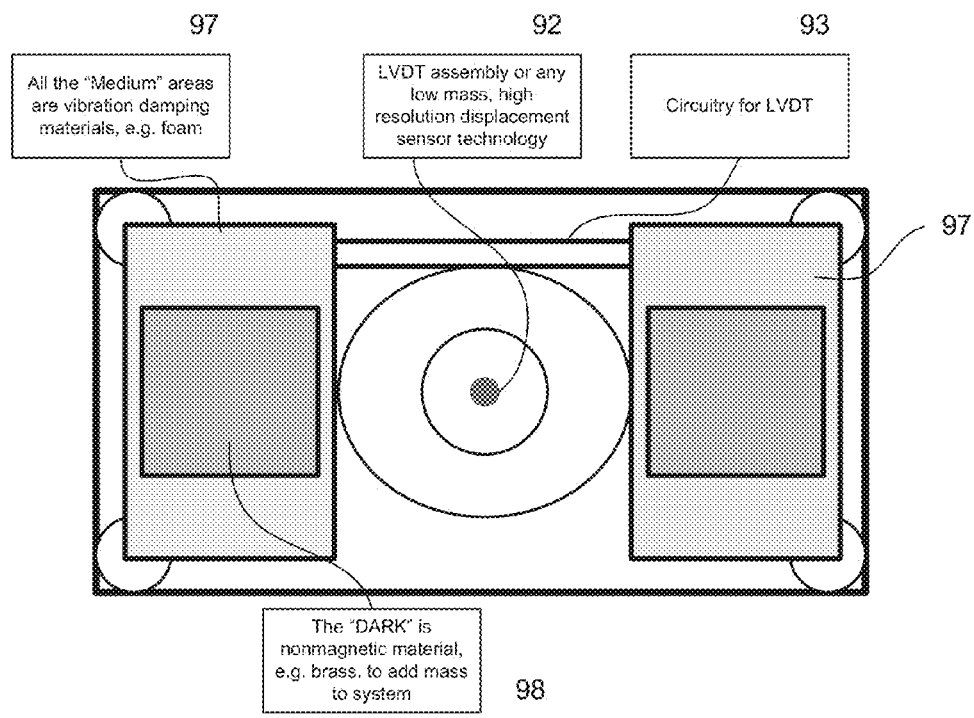
FIGS. 3(A)-(B) are schematic plan and elevation views, respectively, of an embodiment of the present invention acceleration, vibration, and/or deflection module.
Figure 3B:
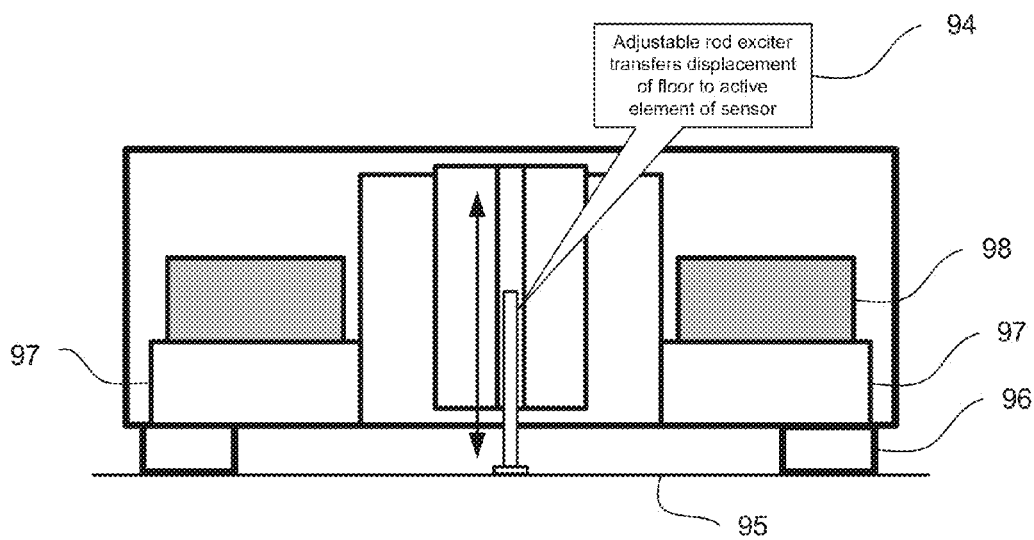

FIGS. 3(A)-(B) are schematic plan and elevation views, respectively, of an embodiment of the present invention acceleration, vibration, and/or deflection module 32. Provided is an embodiment of the present invention acceleration, vibration, and/or deflection module 32 that detects floor acceleration, vibration, and/or deflection to provide acceleration, vibration, and/or deflection signal. The gait sensor 32 transduces the displacement of the floor surface 95 into a waveform signal which can be retained and analyzed. The design employs a linear variable differential transformer (LVDT) 92. The LVDT 92 may also be any low mass, high resolution displacement sensor technology including but are not limited to magnetic coil induction; laser light reflection; changes in Plasmon surface resonance; RF; changes in light due to luminescence; doppler radar; and/or any sensor technology that transduces the minute deflections of the floor induced by gait or falling or dropping of objects. The stationary part of the assembly is suspended by a vibration damping material 96 or structure. The resulting sensor assembly is suspended from a significant mass 98, where that mass is supported by additional damping material 97. The significant mass 98 may also be a nonmagnetic material, for example brass, to add mass to the system or any suitable material. The damping material 97 may also be any suitable vibration damping material or structure, for example foam or the like. The exciter rod 94 of the LVDT extends to the floor surface 95. Whenever there is a displacement of the floor, the moment of inertia of the system is greater than the exciter rod 94, allowing the rod to move in relation to the greater mass, thus deriving a signal from a sensor that does not rely on a different plane (wall) to obtain reference. The adjustable exciter rod 94 is configured to transfer displacement of floor to active element of the sensor.

Figure 3C:
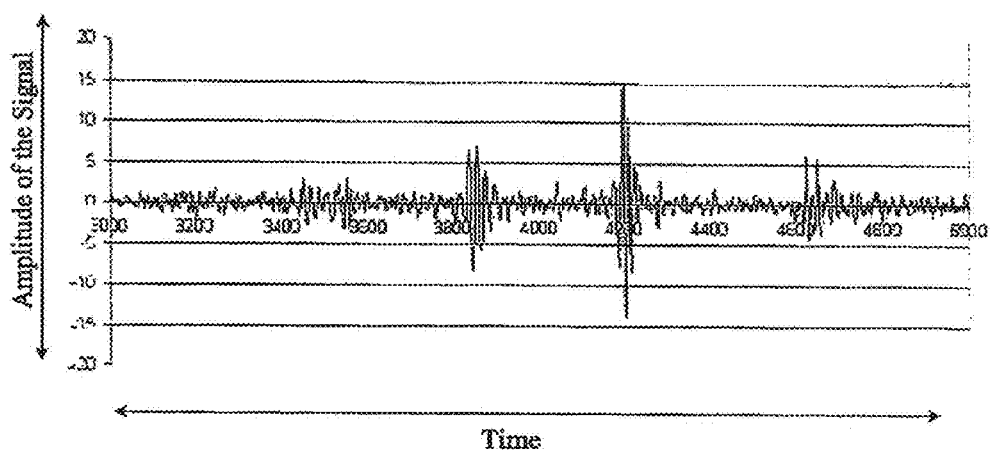
FIGS. 3(C)-(D) show a graphical representation of the "raw" and post processing signals produced in the embodiment of FIGS. 3(A)-(B), wherein the steps are as captured in FIG. 3(D) while the raw signal shows the rich harmonic content as captured in FIG. 3(C).
Figure 3D:
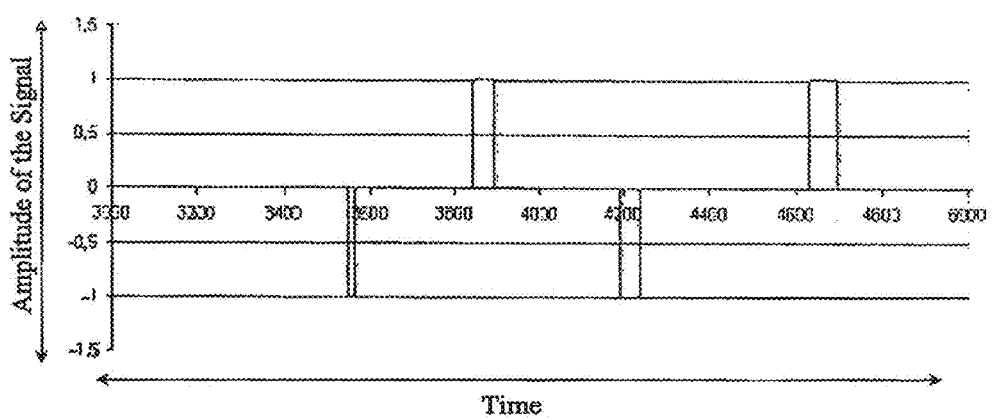

FIGS. 3(C)-(D) show a graphical representation of the "raw" and post processing signals produced in the embodiment of FIGS. 3(A)-(B), wherein the steps are as captured in FIG. 3(D) while the raw signal shows the rich harmonic content as captured in FIG. 3(C).

Example No. 2

Figure 4:
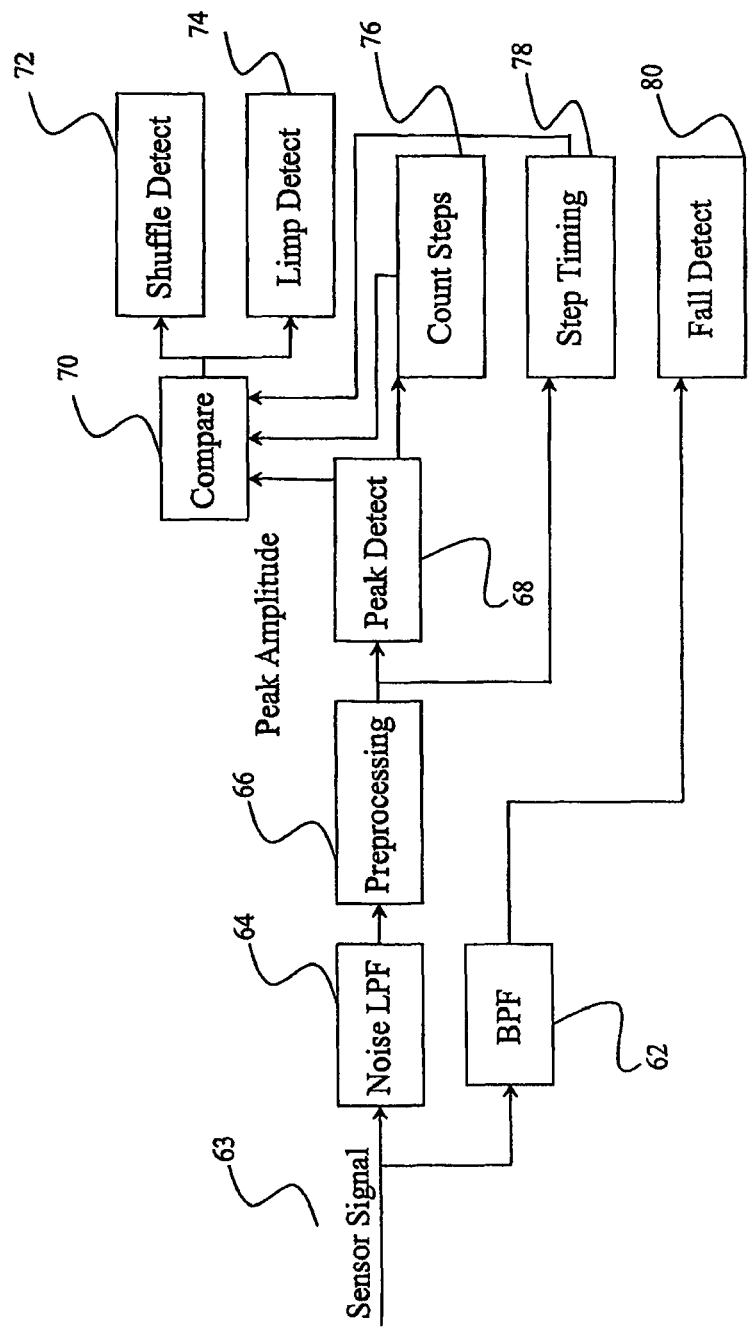
FIG. 4 is a schematic block diagram of an example of the gait monitoring system.

Referring to FIG. 4, FIG. 4 illustrates a schematic a block diagram of an example of an embodiment of the present invention system 61. In the current embodiment, the fall detection is a separate entity from the step counter 78, which allows the calculation of cadence, and from the limp detector 74 and shuffle detector 72. The fall detector consists of a second order Butterworth band-pass filter (about 30 Hz-50 Hz) 62. This filter was tuned to block frequencies generated by different walk modes or dropped objects and to yield the highest output in response to falling people. However, it should be appreciated that other filter designs, including filter type, order and frequencies, may yield similar results. The filter output feeds into an amplifier and comparator 70 to detect falls; the comparator threshold is tuned to detect a low weight human falling about ten feet (or as desired) from the sensor, yet remain insensitive to dropped objects. This reduces potential false alarms without compromising sensitivity to human fall detection.

For detecting step timing and determining limp and shuffle, the original signal is filtered through a second order Butterworth low-pass filter 64 having a cutoff frequency of 3 Hz. However, experts in the art understand that other filter designs, including filter type, order and frequencies, may yield similar results. The filtered signal is processed to produce a large signal that corresponds with footfalls of a walking person. This processing involves taking the derivative of the filtered signal followed by a second stage of low-pass filtering at 10 Hz to remove noise. Similar results can be obtained using a high-gain high-pass filter to approximate the derivative. The processed signal is passed through a peak detector 68 to detect negative peaks in the signal, which correspond with footfalls. Counting the peaks provides a step count and allows the calculation of cadence, defined as the number of steps taken per minute. Step timing information can also be derived by running the processed signal through a zero crossing comparator. Algorithms to compare peak amplitudes, step counts and step timing that provides an accurate estimate of whether a person is limping, shuffling or walking normally.

The above-described system design, including the circuits and the associated algorithms, was simulated on Matlab and Simulink. Real raw sensor data, recorded from a set of experiments carried out on carpeted and uncarpeted wooden floors with a person walking towards and away from the sensor, was input into the simulation model. The results show suitability for a range of different applications.

Example No. 3

Figure 5:
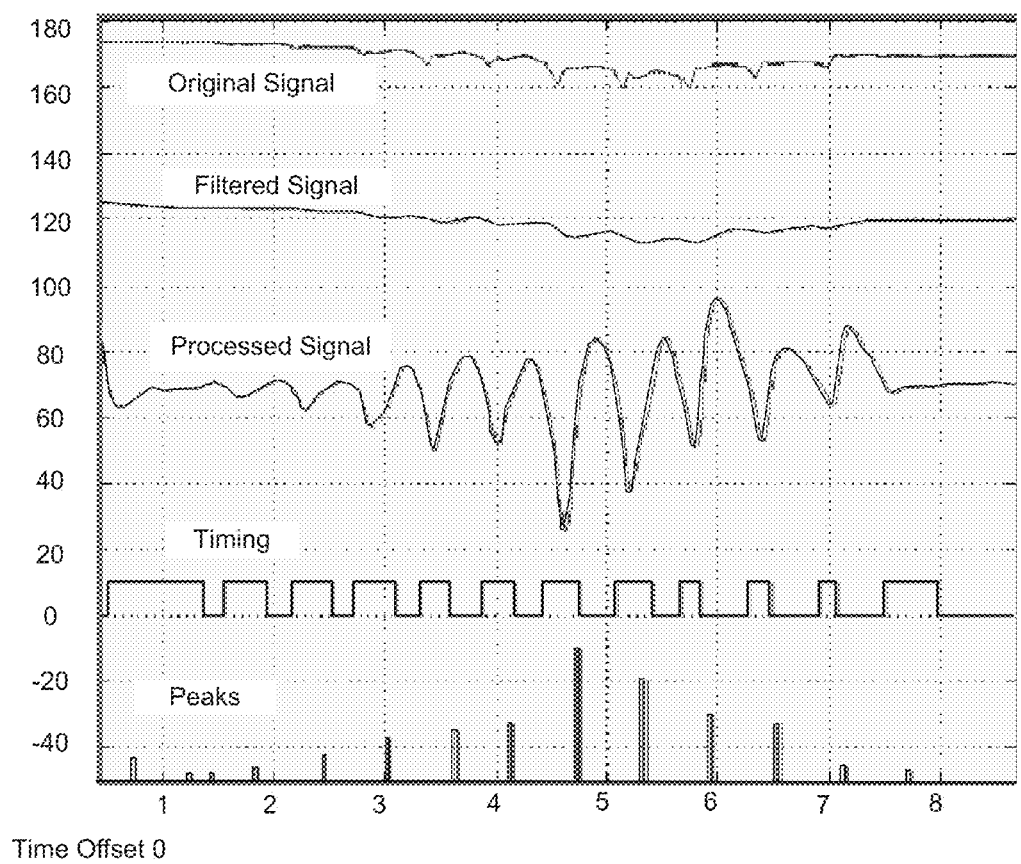
FIG. 5 shows a graphical representation of an example of the results obtained applying an exemplary circuit model to the data obtained from the floor vibration sensor for a normal walk.
Figure 6:
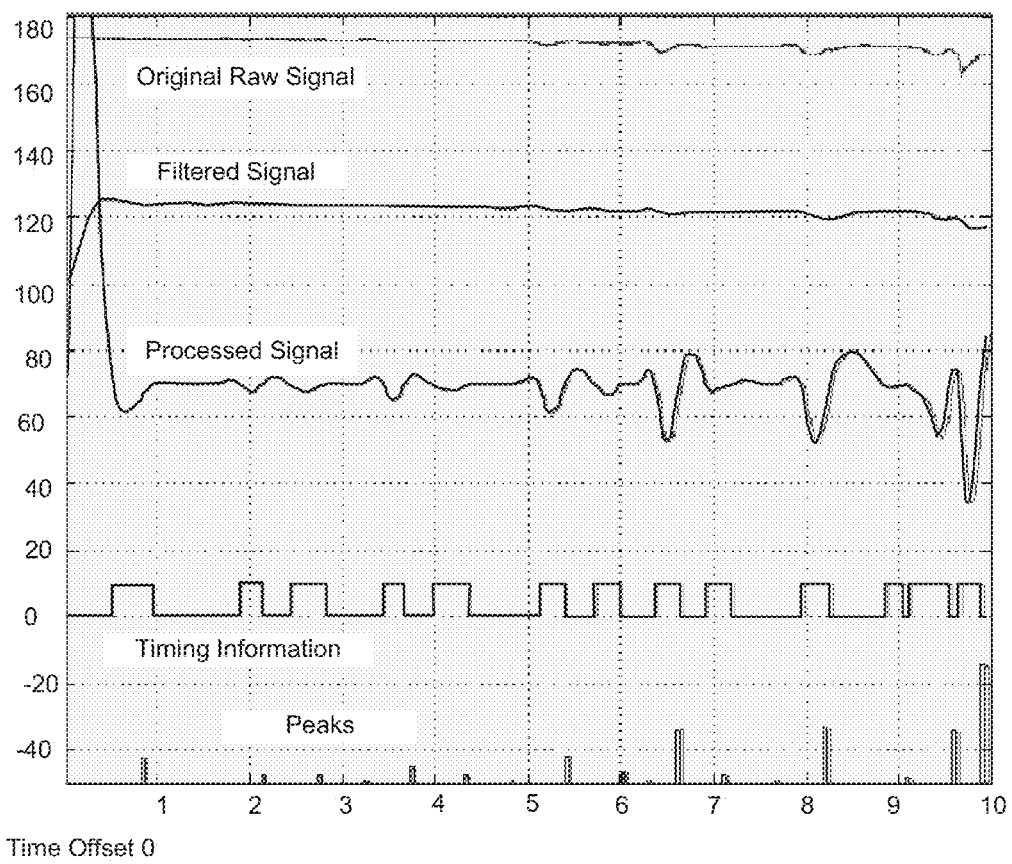
FIG. 6 shows a graphical representation of an example of the results obtained applying an exemplary circuit model to the data obtained from the floor vibration sensor for a limp.
Figure 7:
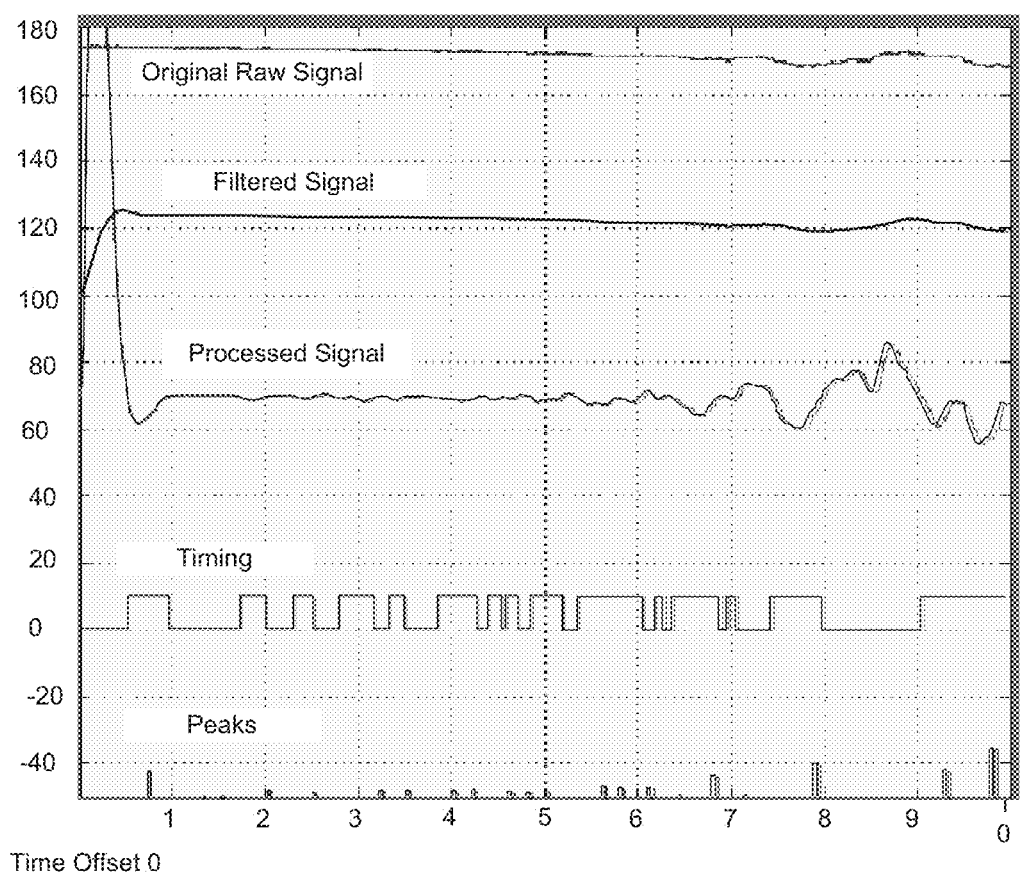
FIG. 7 shows a graphical representation of an example of the results obtained applying an exemplary circuit model to the data obtained from the floor vibration sensor for a shuffle.
Figure 8:
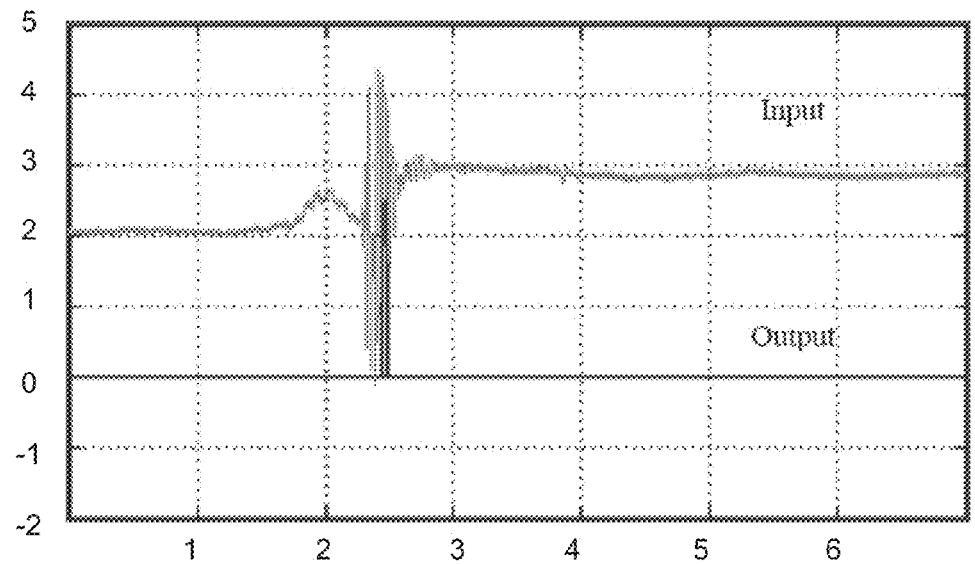
FIG. 8 shows a graphical representation of an example of the results obtained applying an exemplary circuit model to the data obtained from the floor vibration sensor for a fall.

FIG. 5 shows a graphical representation of an example of the results obtained applying an exemplary circuit model to the data obtained from the floor vibration sensor for a normal walk. FIG. 6 shows a graphical representation of an example of the results obtained applying an exemplary circuit model to the data obtained from the floor vibration sensor for a limp. FIG. 7 shows a graphical representation of an example of the results obtained applying an exemplary circuit model to the data obtained from the floor vibration sensor for a shuffle. FIG. 8 shows a graphical representation of an example of the results obtained applying an exemplary circuit model to the data obtained from the floor vibration sensor for a fall.

Turning to FIG. 5, shows FIG. 5 the graphically shows the signals generated by a person walking in a normal gait mode, together with the derived signals throughout the various processing stages in our circuit model. Knowing the location of the sensor during the experiments, it was noted that the amplitude of the detected peaks, corresponding to footfalls, consistently increased when the person walks towards the sensor, and consistently decreased when the person walks away. One can count the steps, by counting the detected peaks, and then calculate cadence based on the time period during which the steps were taken. In this particular experiment, the number of actual steps taken was 13 and our system detected and counted 14 peaks. The difference in the count is a result of falsely counting the first negative peak as a step; this peak is an artifact resulting from filtering data collected off-line. This artifact can be eliminated through the use of a hardware prototype, implementing the circuit design, to filter and process vibration signals in real time. Thus the graph shows that the timing of the steps was fairly regular in normal gait modes.

Turning to FIG. 6, FIG. 6 the graphically shows signals generated from data of a limping person. An alternating pattern for the amplitude of the peaks, high-low-high or low-high-low, was observed; this alternating pattern reflects the difference in percussive pressure applied to the floor by both feet. The amplitude of the peaks still shows an overall trend of increase with the person walking towards the sensor and decrease when walking away from it. However, the difference in alternating amplitudes is higher than the increase or decrease due to proximity to the sensor. Moreover, the alternation pattern is reversed when the person approaches the sensor and walks away. The peaks counted in this case were 16 whereas the actual number of steps taken was only 14. The difference here may also be attributed to the artifacts resulting from filtering data off-line. From the figure, one can observe irregular and skewed step timing in case of limping.

Turning to FIG. 7, FIG. 7 the graphically shows the signal generated by a shuffling subject and the derivations of the signal. From shuffling data, one can observe a large number of low amplitude peaks that have no correlation with each other or proximity to the sensor. In case of shuffling, irregular and skewed step timing signal is also noticed.

Turning to FIG. 8, the methodology included performing extensive experiments with falling objects on both carpeted and uncarpeted wooden floors and a few experiments with falling people only on carpeted floors. Extensive simulations and design iterations allowed the example methodology to successfully differentiate falling objects from falling people through tuning the band pass filter employed to a specific frequency range to increase sensitivity to falling people and to reduce the probability of false alarms resulting from falling objects. In particular, FIG. 8 shows the output of the fall detector successfully triggered by a person, weighing 175 lb., falling 9 feet away from the sensor on a carpeted area of a wooden floor.

Figure 9:
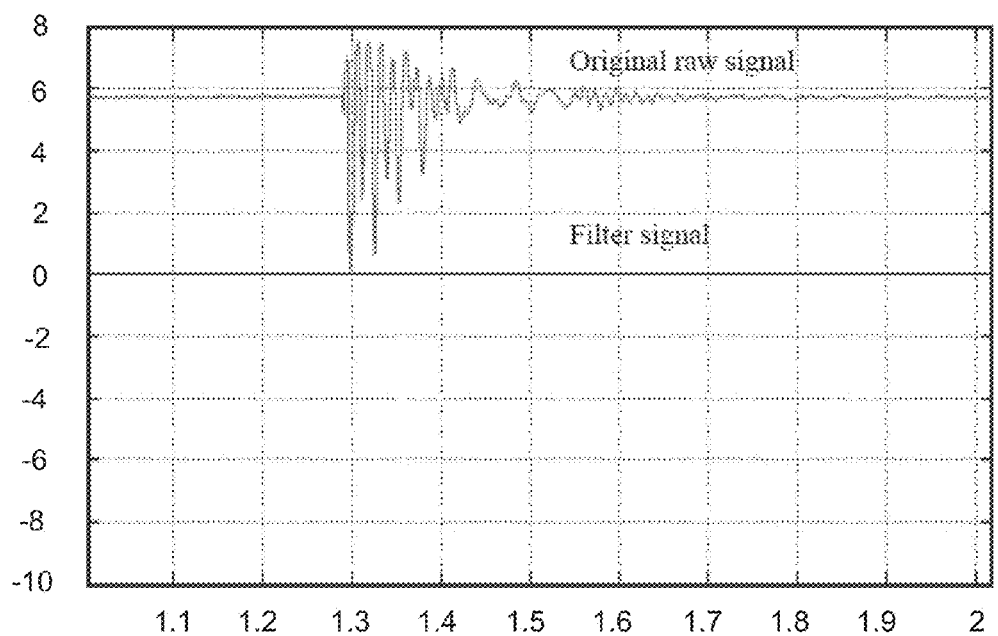
FIG. 9 shows the graphically shows an example demonstrating the fall detector's reduced sensitivity to falling objects.

Turning to FIG. 9, shows FIG. 9 the graphically shows an example demonstrating the fall detector's reduced sensitivity to falling objects. In this experiment an object, weighing 3 lb., was dropped from a height of 1 ft. onto the uncarpeted section of the wooden floor 7.3 ft. away from the sensor.

Next, the method of present invention may be implemented using hardware, software or a combination thereof and may be implemented in one (or part of) or more computer systems or other processing systems, such as personal digit assistants (PDAs) or in communication with the same.

In an example embodiment, the invention was implemented in software running on a general purpose computer or the like. Computer system includes one or more processors. Such processor may be connected to a communication infrastructure (e.g., a communications bus, cross-over bar, or network). The computer system may include a display interface that forwards graphics, text, and other data from the communication infrastructure (or from a frame buffer not shown) for display on the display unit.

The Computer system may also include a main memory, preferably random access memory (RAM), and may also include a secondary memory. The secondary memory may include, for example, a hard disk drive and/or a removable storage drive, representing a floppy disk drive, a magnetic tape drive, an optical disk drive, a flash memory etc. The removable storage drive reads from and/or writes to a removable storage unit in a well known manner. Removable storage unit, represents a floppy disk, magnetic tape, optical disk, etc. which is read by and written to by removable storage drive. As will be appreciated, the removable storage unit includes a computer usable storage medium having stored therein computer software and/or data.

In alternative embodiments, secondary memory may include other means for allowing computer programs or other instructions to be loaded into computer system. Such means may include, for example, a removable storage unit and an interface. Examples of such removable storage units/interfaces include a program cartridge and cartridge interface (such as that found in video game devices), a removable memory chip (such as a ROM, PROM, EPROM or EEPROM) and associated socket, and other removable storage units and interfaces which allow software and data to be transferred from the removable storage unit to computer system.

The computer system may also include a communications interface. Communications interface allows software and data to be transferred between computer system and external devices. Examples of communications interface may include a modem, a network interface (such as an Ethernet card), a serial or parallel communications port, a PCMCIA slot and card, a modem etc. Software and data transferred via communications interface are in the form of signals, which may be electronic, electromagnetic, optical or other signals capable of being received by communications interface. Signals are provided to communications interface 124 via a communications path (i.e., channel). A channel (or any other communication means or channel disclosed herein) carries signals and may be implemented using wire or cable, fiber optics, a phone line, a cellular phone link, an RF link, an infrared link and other communications channels.

In this document, the terms "computer program medium" and "computer usable medium" are used to generally refer to media such as removable storage drive, a hard disk installed in hard disk drive, and signals. These computer program products are means for providing software to computer system. The invention includes such computer program products.

Computer programs (also called computer control logic) are stored in main memory and/or secondary memory. Computer programs may also be received via communications interface. Such computer programs, when executed, enable computer system to perform the features of the present invention as discussed herein. In particular, the computer programs, when executed, enable processor to perform the functions of the present invention. Accordingly, such computer programs represent controllers of computer system.

In an embodiment where the invention is implemented using software, the software may be stored in a computer program product and loaded into computer system using removable storage drive, hard drive or communications interface. The control logic (software), when executed by the processor, causes the processor to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in various programs and programming language known to those skilled in the art.

The following publications, patent applications, and patents are hereby incorporated by reference herein in their entirety:

U.S. Pat. No. 6,360,597 B1 to Hubbard, Jr., entitled "In-Shoe Remote Telemetry Gait Analysis System;"
U.S. Pat. No. 6,301,964 B1 to Fyfe et al., entitled "Motion Analysis System;"
U.S. Pat. No. 6,168,569 B1 to McEwen et al., entitled "Apparatus and Method for Relating Pain and Activity of a Patient;"
U.S. Pat. No. 6,145,389 to Ebeling et al., entitled "Pedometer Effective for both Walking and Running;"
U.S. Pat. No. 6,095,991 to Krausman et al., entitled "Ambulatory Body Position Monitor;"
U.S. Pat. No. 6,010,465 to Nashner, entitled "Apparatus and Method for Characterizing Gait;"
U.S. Pat. No. 5,952,585 to Trantzas et al., entitled "Portable Pressure Sensing Apparatus for Measuring Dynamic Gait Analysis and Method of Manufacture;"
U.S. Pat. No. 5,919,149 to Allum, entitled "Method and Apparatus for Angular Position and Velocity Based Determination of Body Sway for the Diagnosis and Rehabilitation of Balance and Gait Disorders;"
U.S. Pat. No. 5,831,937 to Weir et al., entitled "Portable Ranging System for Analyzing Gait;"
U.S. Pat. No. 5,807,283 to Ng, entitled "Activity Monitor;"
U.S. Pat. No. 5,623,944 to Nashner, entitled "Method for Characterizing Gait;"
U.S. Pat. No. 5,511,571 to Adrezin et al., entitled "Method and Apparatus for Gait Measurement;"
U.S. Pat. No. 5,511,561 to Wanderman et al., entitled "Gait Cycle Force Monitor,"
U.S. Pat. No. 5,485,402 to Smith et al., entitled "Gait Activity Monitor;"
U.S. Pat. No. 5,474,087 to Nashner, entitled "Apparatus for Characterizing Gait;"
U.S. Pat. No. 5,337,757 to Jain et al., entitled "Device for Inducing and Registering Imbalance;"
U.S. Pat. No. 5,186,062 to Roost, entitled "Method of Investigating the Gait of a Living Being;"
U.S. Pat. No. 5,138,550 to Abraham et al., entitled "Device for Monitoring the Gait in Particular of a Horse and Monitoring System to Which it is Applied;"
U.S. Pat. No. 4,813,436 to Au, entitled "Motion Analysis System Employing Various Operating Modes;"
U.S. Pat. No. 4,651,446 to Yukawa et al., entitled "Electronic Pedometer;"
U.S. Pat. No. 4,600,016 to Boyd et al., entitled "Method and Apparatus for Gait Recording and Analysis;"
U.S. Pat. No. 4,510,704 to Johnson, entitled "Boot or Shoe Incorporating Pedometer or to the Like;"
U.S. Pat. No. 4,387,437 to Lowery et al., entitled "Runners Watch;"
U.S. Pat. No. 4,371,945 to Karr et al., entitled "Electronic Pedometer;"
U.S. Pat. No. 4,223,211 to Allsen et al., entitled "Pedometer Devices;"
U.S. Pat. No. 4,192,000 to Lipsey, entitled "Electronic Calorie Counter;"
U.S. Pat. No. 4,144,568 to Hiller et al., entitled "Exercise Recorder;"
U.S. Pat. No. 6,696,956 B1 to Uchida et al., entitled "Emergency Dispatching System;"
U.S. Pat. No. 6,687,424 B1 to Gerdt et al., entitled "Sensing Pad Assembly Employing Variable Coupler Fiberoptic Sensor;"
U.S. Pat. No. 6,659,968 B1 to McClure, entitled "Activity Monitor for Pain Management Efficacy Measurement;"
U.S. Pat. No. 6,640,212 B1 to Rosse, entitled "Standardized Information Management System for Long-Term Residence Facilities;"
U.S. Pat. No. 6,571,193 B1 to Unuma et al., entitled "Method, Apparatus and System for Recognizing Actions;"
U.S. Pat. No. 6,524,239 B1 to Reed et al., entitled "Apparatus for Non-Intrusively Measuring Health Parameters of a Subject and Method of Use Thereof;"

U.S. Pat. No. 6,515,586 B1 to Wymore, entitled "Tactile Tracking Systems and Methods;"

U.S. Pat. No. 6,463,187 B1 to Baruch et al., entitled "Variable Coupler Fiberoptic Sensor and Sensing Apparatus Using the Sensor;"

U.S. Pat. No. 6,221,010 B1 to Lucas, entitled "Home Medical Supervision and Monitoring System;"

U.S. Pat. No. 6,221,010 B1 (Certificate of Correction) to Lucas, entitled "Home Medical Supervision and Monitoring System;"

U.S. Patent Application Publication 2003/0199771 A1 to Baruch et al., entitled "Apparatus and Method for Measuring Pulse Transit Time;" and U.S. Patent Application Publication 2002/0107649 A1 to Takiguchi et al., entitled "Gait Detection System, Gait Detection Apparatus, Device, and Gait Detection Method."

In summary, the present invention gait monitor system and method described herein can provide various basic gait parameters including step count, cadence, and step duration, in addition to its ability to distinguish between normal, limping and shuffling gait modes as well as but not limited to physical forces that are currently known in gait such as heel impact, roll from heel to toe, toe-off, heel rotation, forces generated when the toes push off the floor to get locomotion (e.g. gastricnemeous contraction), knee flexure, hip rotation, and pelvis swivel, etc. These individual force generators should also be integrated into the amount of forward motion that is generated, versus the amount of motion that is spent lifting the body. However, this gait monitor may be augmented with additional sensors, e.g. beam break at the beginning and end of a corridor to estimate average walking velocity (with the distance between the beams known or determined); this enables the calculation of additional gait characteristics such as average step length and average stride length. These parameters can additionally be used to detect various gait anomalies.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of the appended claims. For example, regardless of the content of any portion (e.g., title, section, abstract, drawing figure, etc.) of this application, unless clearly specified to the contrary, there is no requirement for any particular described or illustrated activity or element, any particular sequence of such activities, any particular size, speed, dimension or frequency, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Accordingly, the descriptions and drawings are to be regarded as illustrative in nature, and not as restrictive.

We claim:

1. A gait monitoring system for monitoring gait characteristics of a subject, said system comprising:

a sensor module including a sensor configured to touch an upper surface of a floor, the sensor module configured to while the sensor is touching the upper surface of the floor detect at least one of floor acceleration, floor vibration, and floor deflection and to provide at least one of an acceleration, vibration, and deflection signal, wherein the subject can walk on the upper surface of the floor in proximity to said sensor; and a processor configured to:

analyze the acceleration, vibration, and deflection signal and to determine gait characteristics based on the signal;

determine the gait characteristics based on the at least one signal from a single sensor module; and detect a fall of a human being by distinguishing between steps of the human being and the fall of the human being and comparing data based on the signal to a threshold, wherein the threshold is adjustable.

2. The system of claim 1, further comprising an output module for receiving data indicative of the gait characteristics.

3. The system of claim 1, wherein said sensor module and a processor module are in wireless communication.

4. The system of claim 1, wherein said threshold is adjusted remotely.

5. The system of claim 1, further comprising a rate-of-travel detector to determine the rate-of-travel of the subject.

6. The system of claim 1, wherein the gait characteristics of the subject includes at least two of step count, pace, normal gait condition, limp, shuffle, and falls.

7. The system of claim 1, further comprising a second processor module, wherein said second processor module is configured to analyze the gait characteristics, pattern recognition, and identification determination data, wherein the identification determination data associates gait characteristics with a particular subject.

8. The system of claim 1, further comprising a fall module configured to initiate an alert call regarding a fall based on the data.

9. The system of claim 8, wherein the alert call is at least partly transmitted via a wireless communication to at least one of a designated care provider and an emergency service.

10. A method for monitoring gait characteristics of a subject, said method comprising:

detecting at least one of a floor acceleration, a floor vibration, and a floor deflection to provide at least one of an acceleration, vibration, and deflection signal, wherein said detecting is provided by a sensor module touching an upper surface of a floor, and wherein the subject walks on the upper surface of the floor in proximity to said sensor module;

using a processor:

analyzing the at least one signal; and determining gait characteristics based on the at least one signal, wherein the gait characteristics are determined based on the at least one signal from a single sensor module; and the analyzing further includes detecting a fall of a human being by distinguishing between steps of the human being and the fall of the human being and comparing data based on the signal to a threshold, wherein the threshold is adjustable.

11. The method of claim 10, further comprising outputting data indicative of the gait characteristics.

12. The method of claim 10, further comprising detecting a rate-of-travel of the subject.

13. The method of claim 10, further comprising automatically identifying signals indicative of a human body falling to determine fall data.

14. The method of claim 10, further comprising remotely adjusting the threshold.

15. The method of claim 10, further comprising initiating an alert call regarding a fall based on the data.

16. The method of claim 15, wherein the alert call is at least partly transmitted via a wireless communication to at least one of a designated care provider and an emergency service.

17. A computer program product comprising non-transitory computer usable medium having computer logic embedded thereon for enabling at least one processor in a computer system to monitor gait characteristics of a subject, said computer logic configured to cause the computer system to:
receive at least one of a floor acceleration, a floor vibration, and a floor deflection signal, wherein said at least one signal is provided by a sensor module touching an upper surface of a floor, and wherein the subject can walk on the upper surface of the floor in proximity to said sensor module; and
analyze the at least one signal; and
determine gait characteristics based on the at least one signal,
wherein, the gait characteristics are determined based on the at least one signal from a single sensor module; and
the analyzing further including detecting a fall of a human being by distinguishing between steps of the human being and the fall of the human being and comparing data based on the signal to a threshold wherein the threshold is adjustable.

18. The computer program product of claim 17, wherein the threshold is adjusted remotely.

19. The computer program product of claim 17, further configured to initiate an alert call regarding a fall based on the data.

20. The computer program product of claim 19, wherein said alert call is at least partly transmitted via a wireless communication to at least one of a designated care provider and an emergency service.

* * * * *